United States Patent [19]

Machold et al.

[11] Patent Number: 4,976,720

[45] Date of Patent: Dec. 11, 1990

[54] VASCULAR CATHETERS

[75] Inventors: Timothy R. Machold, Moss Beach; Craig E. Mar, Fremont; Richard L. Mueller, Jr., Mountain View; John P. Shanahan, San Jose, all of Calif.

[73] Assignee: Advanced Cardiovascular Systems, Inc., Santa Clara, Calif.

[21] Appl. No.: 220,563

[22] Filed: Jul. 18, 1988

Related U.S. Application Data

[63] Continuation-in-part of Ser. No. 646, Jan. 6, 1987, abandoned, and a continuation-in-part of Ser. No. 650, Jan. 6, 1987, Pat. No. 4,771,778.

[51] Int. Cl.⁵ ............................................. A61M 29/02
[52] U.S. Cl. ..................................... 606/194; 604/95; 604/96
[58] Field of Search ........ 128/657; 658, 604/96, 164, 604/166, 170, 265, 280; 606/194, 192

[56] References Cited

U.S. PATENT DOCUMENTS

| 4,538,622 | 9/1985 | Samson et al. |
| 4,582,181 | 4/1986 | Samson |
| 4,616,653 | 10/1986 | Samson et al. |
| 4,641,654 | 2/1987 | Samson et al. ........................ 604/95 |
| 4,646,742 | 3/1987 | Packard et al. ...................... 604/102 |
| 4,771,778 | 9/1988 | Mar ........................................ 604/96 |
| 4,793,350 | 12/1988 | Mar et al. .............................. 604/96 |

FOREIGN PATENT DOCUMENTS

| 0165727 | 4/1985 | European Pat. Off. . |
| 0213751 | 2/1987 | European Pat. Off. . |
| 0231601 | 6/1987 | European Pat. Off. . |
| 0231725 | 8/1987 | European Pat. Off. . |
| WO86/06285 | 11/1986 | PCT Int'l Appl. . |
| 2172205A | 2/1986 | United Kingdom . |

Primary Examiner—Stephen C. Pellegrino
Attorney, Agent, or Firm—Fulwider, Patton & Utecht

[57] ABSTRACT

The invention is directed to a very low-profile dilatation catheter having an inner tubular member with an inner lumen with a diameter of not more than 0.003 inch (0.076 mm) greater than the diameter of a guidewire disposed therein. Preferably, the inner diameter of the tubular member is less than 0.015 inch (0.381 mm). The inner member may be formed of a thin-walled tubing such as polyimide tubing having a wall thickness less than 0.003 inch (0.076 mm). Polyimide tubing is also preferably employed as the tubular member in low-profile steerable dilatation catheters wherein the guide elements thereof are fixed within the catheter.

11 Claims, 2 Drawing Sheets

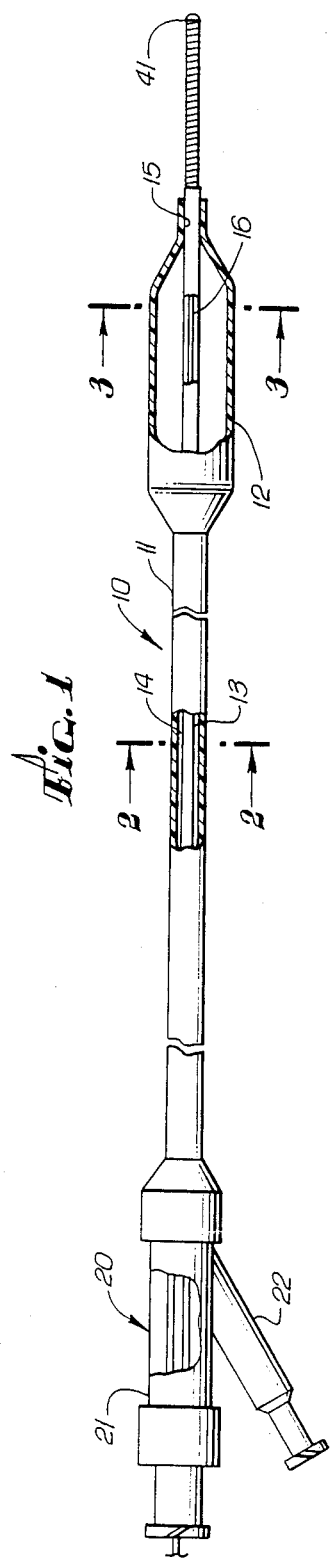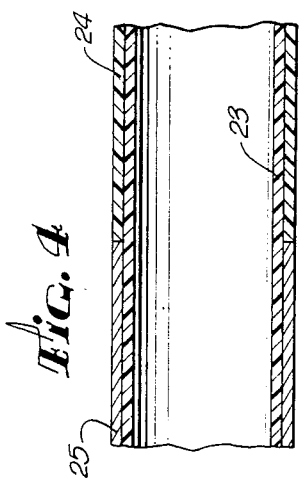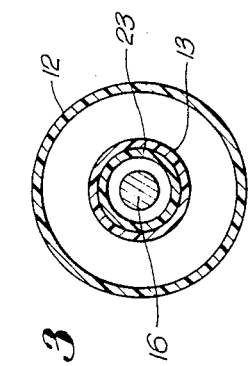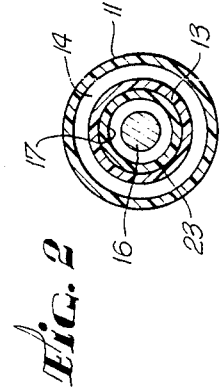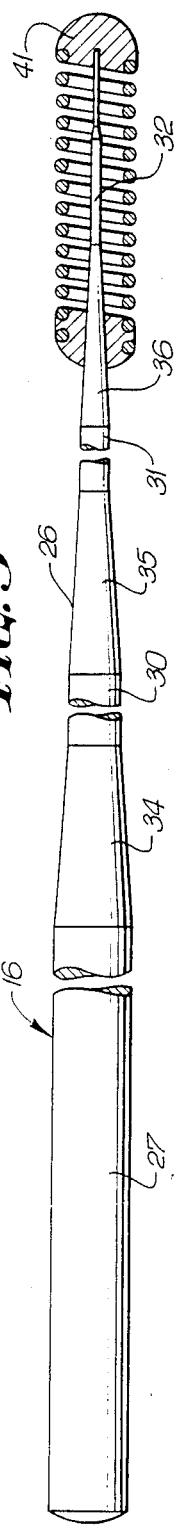

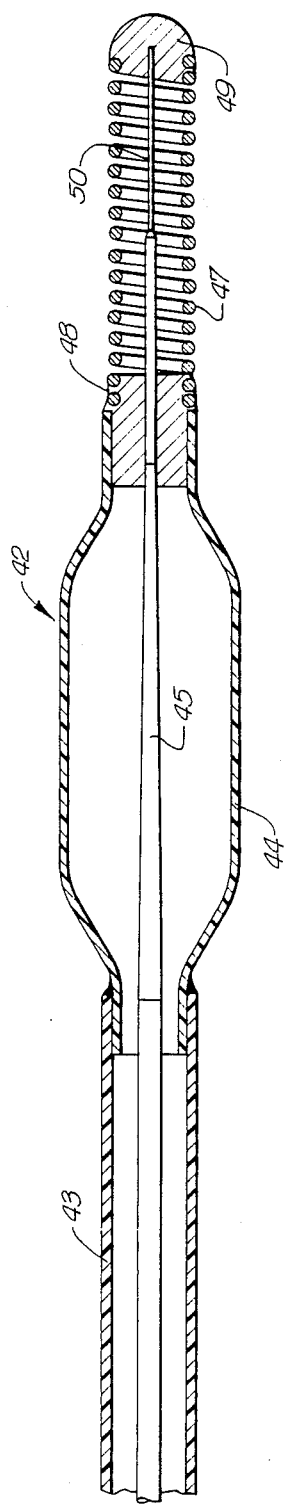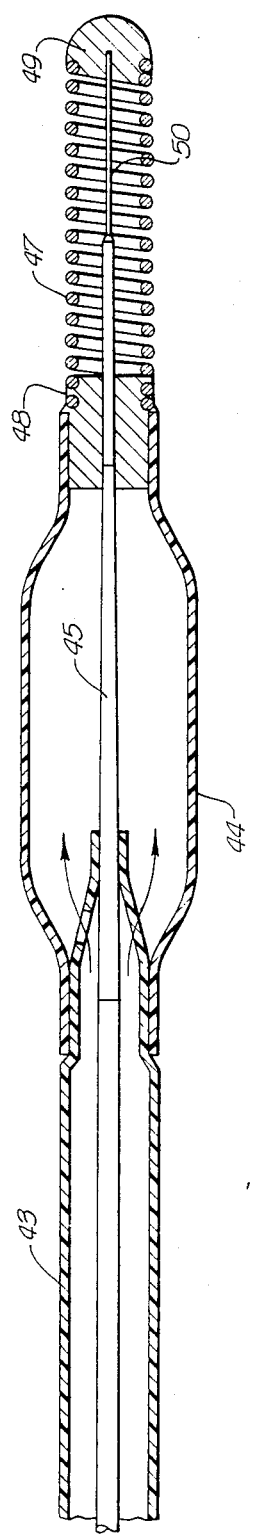

VASCULAR CATHETERS

RELATED APPLICATIONS

This application is a continuation-in-part of applications Ser. No. 000,646, filed Jan. 6, 1987 now abandoned, and Ser. No. 000,650, filed Jan. 6, 1987, now U.S. Pat. No. 4,771,778.

BACKGROUND OF THE INVENTION

This invention generally relates to vascular catheters and particularly to catheters for vascular procedures such as percutaneous transluminal coronary angioplasty (PTCA).

In typical PTCA procedures, a guiding catheter having a preformed distal tip is percutaneously introduced into the cardiovascular system of a patient and advanced therein until the distal tip thereof is in the ostium of the desired coronary artery. A guidewire is introduced through the guiding catheter and advanced into the patient's coronary vasculature until the distal end of the guidewire crosses the lesion to be dilated. A dilatation catheter having an inflatable balloon on the distal portion thereof is advanced over the previously introduced guidewire, with the guidewire slidably disposed within an inner lumen of the dilatation catheter, until the dilatation balloon is properly positioned across the lesion. Once in position across the lesion, the flexible, relatively inelastic balloon is inflated to a predetermined size with radiopaque liquid at relatively high pressures to radially compress the atherosclerotic plaque of the lesion against the inside of the artery wall. The balloon is then deflated so that the dilatation catheter can be removed and blood flow resumed through the dilated artery.

Further details of angioplasty procedures and the devices used in such procedures, can be found in U.S. Pat. No. 4,332,254 (Lundquist); U.S. Pat. No. 4,323,071 (Simpson-Robert); U.S. Pat. No. 4,439,185 (Lundquist); U.S. Pat. No. 4,468,224 (Enzmann et al.) U.S. Pat. No. 4,516,972 (Samson); U.S. Pat. No. 4,538,622 (Samson et al.); and U.S. Pat. No. 4,616,652 (Simpson) which are hereby incorporated herein in their entirety.

It is generally desirable to make the deflated profile of the dilatation catheter as small as possible because a smaller profile allows a catheter to pass through tighter lesions and to be advanced much further into the patient's coronary anatomy. However, if the diameter of the guidewire is reduced to reduce the profile of the catheter, the ability of the guidewire to transmit torsional and axial forces is likewise reduced. Heretofore, movable guidewires utilized in coronary angioplasty typically have been on the order of 0.012–00.018 inch (0.305–0.457 mm) in diameter. Attempts have been made to use smaller diameter movable guidewires in angioplasty procedures, but such smaller diameter guidewires frequently were unable to effectively transmit torque for steering the guidewire from the proximal to the distal ends, and, in many instances, they did not have the pushability to be readily advanced through the tortuous coronary vasculature without buckling or kinking.

Heretofore, attempts have also been made to reduce the profile of dilatation catheters by reducing the wall thickness of the tubular members which make up the catheters. However, as with reducing the diameter of the guidewire, there is a limit on how much the wall thickness of the tubular members can be reduced without detrimentally affecting the performance of the catheter.

What has been needed and heretofore unavailable is a dilatation catheter assembly which has a substantial reduction in profile with essentially no loss in performance characteristics. The present invention satisfies that need.

SUMMARY OF THE INVENTION

This invention is directed to an improved low-profile balloon dilatation catheter assembly which is particularly useful with a small diameter guidewire.

A vascular catheter in accordance with the invention generally comprises an elongated tubular member having an inner lumen extending therethrough which is adapted to receive a guidewire and which has an inner diameter of not more than 0.003 inch (0.076mm) greater than the outside diameter of the guidewire over a substantial portion of the lumen length. The inner lumen preferably has a diameter of less than 0.015 inch (0.381 mm). In this manner, the inside surface of the inner lumen is close enough to a guidewire disposed therein to provide support to the guidewire and to prevent the buckling thereof when the guidewire is subjected to axial forces, such as when the guidewire is advanced through a patient's vasculature. Moreover, by maintaining a lubricious surface on the inner wall of the tubular member which defines the inner lumen, contact friction between the lumen surface and the guidewire can be reduced substantially and thereby allow a more effective transmission of steering torque from the proximal to the distal extremities of the guidewire. The invention is particularly directed to dilatation catheters having inflatable balloons on the distal ends thereof.

In a presently preferred embodiment, the inner tubular member is a longitudinally flexible but diametrically rigid tubular element formed of polyimide. This polymeric material provides a tubular member having the strength and flexibility of prior tubular members formed from materials such as polyethylene, polyvinylchloride and polyurethane but with substantially smaller wall thickness. For example, the polyethylene tubing typically used for dilatation catheters has a nominal wall thickness of about 0.005 inch (0.127 mm). Polyimide tubing having a nominal wall thickness of about 0.001 inch (0.025 mm) will provide essentially the same strength and flexibility as the typical polyethylene tubing, but the thin wall thereof provides for a reduction of 0.008 inch (0.203 mm) in profile, which can amount to a reduction up to 40% or more in the outer diameter of the polyethylene tubing.

In another embodiment of the invention, thin-walled polyimide tubing is utilized as the tubular member in a low-profile steerable dilatation catheter wherein a guidewire or guiding element is fixed within the dilatation catheter. In this embodiment, the proximal end of an inflatable balloon element is secured to the distal end of the polyimide tubing with the inner lumen of the polyimide tubing adapted to direct inflating fluid to the interior of the balloon. A guiding element extends through the interior of the balloon and the distal end of the balloon is sealed about the guiding element projecting therethrough to prevent the loss of inflating liquid. A helical coil is disposed about the portion of the guide element which projects through the distal end of the balloon and is secured thereto by brazing, soldering, or other suitable means. The guide element may extend proximally through the polyimide tubing to the proximal end of the catheter and be provided with a torquing knob at the proximal end in a conventional manner. Alternatively, the proximal end of the guide element may be secured to the distal end of the polyimide tubing with the proximal end of the polyimide tubing provided with torquing means.

Further details of low-profile steerable dilatation catheters can be found in U.S. Pat. No. 4,582,181 and U.S. Pat. Application Ser. No. 000,650, filed Jan. 6, 1987, which are hereby incorporated herein in their entirety by reference thereto.

The present invention provides for a substantial reduction in the profiles of a wide variety of dilatation catheters with no loss in steering capabilities or catheter performance. Moreover, the invention allows for the use of guide wires with much smaller diameters.

These and other advantages of the invention will become more apparent from the following detailed description of the invention when taken in conjunction with the accompanying exemplary drawings.

BRIEF DESCRIPTION OF THE DRAWINGS

FIG. 1 is a side elevational view, partially in section, of a dilatation catheter assembly embodying features of the invention;

FIG. 2 is an enlarged cross-sectional view taken along line 2—2 of FIG. 1;

FIG. 3 is an enlarged cross-sectional view taken along line 3—3 of FIG. 1;

FIG. 4 is an enlarged side elevational view of the guidewire shown in FIG. 1;

FIG. 5 is a longitudinal cross-sectional view of a low-profile steerable dilataton catheter embodying features of the invention; and FIG. 6 is a longitudinal cross-sectional view of an alternate low-profile steerable dilatation catheter embodying features of the invention.

FIG. 7 is a longitudinal cross-sectional view of another embodiment of a low profile steerable dilation catheter embodying features of the invention.

DETAILED DESCRIPTION OF THE INVENTION

FIG. 1 illustrates a catheter 10 embodying features of the invention which has an axially extending outer tubular member 11 with a flexible, relatively inelastic inflatable balloon element 12 near the distal end thereof. An inner tubular member 13 extends coaxially within the outer tubular member 11 and defines an annular passageway 14 therebetween which connects in fluid communication the interior of balloon 12 with a source of inflation fluid at the proximal end of the catheter 10. The distal end portions of the tubular members 11 and 13 are joined together at location 15 by suitable means such as heat sealing or by adhesive to seal the distal end of the balloon 12 and prevent the loss of inflation fluid therefrom. A passageway or other suitable means (not shown) is provided which is in fluid communication with the interior of balloon 12 to allow the passage of air out of the distal portion of the catheter but will prevent the passage of inflating liquid. This allows trapped air to be vented from the balloon 12 as it is filled with inflating liquid. A guidewire 16 extends through an inner lumen 17 in the inner tubular member 13. The diameter of inner lumen 17 is slightly larger than the diameter of the guidewire 16 over a substantial portion of the length thereof.

A two-arm adapter 20 is secured to the proximal end of the catheter 10. Guidewire 16 passes through arm 21, and arm 22 is adapted to be connected in fluid communication with annular passageway 14 and a source of inflation fluid (not shown).

Outer tubular member 11 may be fabricated of a relatively flexible material such as a low-density polyethylene. However, to facilitate advancement over guidewire 16 in a patient's vasculature, the proximal end portion of tubular member 13 may be provided with a stiffener sleeve (not shown) formed of a more rigid material such as a higher density polyethylene, such as is described in copending application Ser. No. 903,029, filed Sept. 2, 1986, assigned to the present assignee. The outer tubular member 12 and the tubular stiffener sleeve may be secured together by heat sealing or other suitable means to form a laminated tubular structure which has a relatively flexible distal portion and a relatively stiff proximal portion.

The inner tubular member 13, which is shown in FIGS. 1–3, has an inner lumen 17 extending therethrough which is adapted to receive a guidewire 16 therein. The inner lumen 17 has a diameter which is not more than about 0.003 inch (0.076 mm) greater than the outer diameter of guidewire 16 in order to provide support to the guidewire, particularly when the guidewire has a relatively small diameter, e.g., less than 0.012 inch (0.305 mm). Preferably, the diametric size differential between inner lumen 17 and the guidewire 16 ranges from about 0.0005 to about 0.003 inch (0.013 mm to 0.076 mm) to provide maximum support to the relatively thin guidewire 16 to facilitate the transmission of both torsional and axial forces through the guidewire to enhance its steerability and pushability without buckling of the wire. In a presently preferred embodiment the diameter of the inner lumen 17 is less than 0.015 inch (0.38 mm) and the guidewire disposed therein has a diameter from about 0.006 to less than 0.012 inch (0.152–305 mm). The smaller diameter guidewires are useful in small arteries in the coronery and cerebral area.

The inner tubular member 13 is provided with a lubricious inner coating or layer 23 such as polytetrafluoroethylene to reduce the friction with the guidewire. The outer surface of the guidewire 16 may also be provided with a similar lubricious coating. The polytetrafluoroethylene (Teflon) layer or coating provides an additional advantage of providing increased lubricity with increased pressure. Thus, when the guidewire 16 moves within the lumen 17, it presses against the Teflon lining of the inner lumen 17 which increases the lubricity of the material, thereby reducing the chances of binding the guidewire within inner lumen 17. Further, while the inner lumen 17 of inner tubular member 13 supports the guidewire 16, the guidewire in turn also supports the inner tubular member 13 and the rest of the catheter assembly 10. Thus, when the catheter 10 is advanced across a lesion, most of the axial force applied to the proximal end of the catheter goes into pushing the distal end across the lesion and not into the buckling or crumpling of the catheter or to overcome the contact friction within the lumen 17.

In accordance with one presently preferred embodiment of the invention, all or a substantial part of inner tubular member 13 is formed from relatively thin-walled tubing of polyimide. One presently preferred thin-walled polyimide tubing is the MicroBore TM tubing manufactured by PolyMicro Technologies in Phoenix, Ariz. Another desirable tubing is manufactured from Matrimid ™ 5218 from Ciba-Geigy Corp. of Hawthorn, N.Y. The polyimide tubing may be formed with an inner lubricious lining of polytetrafluoroethylene which may be formed integral therewith or formed as a lining within the tubing. Further information regarding polyimide material may be found in A. Landis, "Commercial Polyimides", *Handbook of Thermoset Plastics*, Chapter 8, Edited by Sidney H. Goodman (1986), and E. Sacher, "A Reexamination of Polyimide Formation," *J. of Macromolecular Science-Physics*, Vol. B25, No. 4(1986) pp 405–418, which are hereby incorporated by reference. The polyimide tubing has a wall thickness of about less than 0.003 inch (0.076 mm), preferably within the range of about 0.00075 to about 0.0015 inch (0.0191 mm to 0.0381 mm), to provide mechanical and physical properties comparable to the conventionally used polyethylene and polyvinylchloride tubular products which have wall thicknesses many times thicker (e.g., 0.005 inch).

A segment of another presently preferred embodiment is illustrated in FIG. 4. As shown, it comprises a relatively long distal portion 24 of flexible polymeric material, such as a conventional low-density polyethylene and a relatively short proximal portion 25 of longitudinally flexible but diametrically rigid material, such as stainless steel hypotube. Preferably, both the proximal and distal portions have a Teflon lining 23, as shown. The stainless steel hypotube in the proximal portion 25 of inner tubular member 13 greatly increases the ability of the catheter to track over a guidewire by transferring force from the unsupported portion of the catheter shaft outside the guiding catheter down the shaft to the catheter tip. In this embodiment, with an overall catheter length typically about 130–150 cm, the stainless steel hypotube would extend for the first 30–50 cm of the inner tubular member 13.

FIG. 5 illustrates guidewire 16 which is suitable for use with the catheter 10. The guidewire 16 generally comprises a relatively thin stainless steel wire with a short tapered distal portion 26 and a relatively long proximal portion 27, the latter longer portion having a diameter preferably of about 0.006 to about 0.010 inch (0.152 mm–0.254 mm). The guidewire 16 may also be provided with a thin Teflon coating (not shown) of about 0.0005 to about 0.001 inch (0.013 to 0.025 mm). The tapered distal portion 26 has four sections 30–33 of progressively smaller cross-sectional dimensions with gentle tapers 34–36 between the progressively smaller sections. The last section 33 is preferably flattened. In a typical embodiment, the guidewire 16 has an overall length of about 175 cm. The proximal portion 25 has a length of about 140 cm and an outer diameter of about 0.010 inch (0.254 mm), section 30 has a length of about 7 cm and a diameter of about 0.008 inch (0.203 mm), section 31 has a length of about 18 cm and a diameter of about 0.006 inch (0.152 mm), section 33 has a length of about 1 cm and a diameter of about 0.004 inch (0.102 mm), and the flattened section 35 has a length of about 0.75 cm and a thickness of about 0.0008 inch (0.02 mm). Each of the tapered sections 34–36 is about 3 cm in length and provides a reduction in diameter of about 0.002 inch (0.051 mm) over this length. This guidewire is particularly suitable for use in accordance with the invention with a dilatation catheter having an inner lumen of less than about 0.013 inch (0.330 mm). Helical coil 40 is coaxially disposed about the distal portion 24 of the guidewire 16 with the distal tip of flattened section 33 being secured to plug 41 which is preferably made of radiopaque material. The proximal end of the coil 40 is secured to the tapered section 36 by brazing, soldering, or other suitable means. The coil 40 typically has a length of about 1.5 cm and in one presently preferred embodiment, is fabricated from a platinum wire having a diameter on the order of 0.0025 inch (0.064 mm) to make the tip of the coil visible under fluoroscopic examination.

Other embodiments of the invention are shown in FIGS. 6 and 7 which illustrate low-profile steerable dilatation catheters. With respect to the embodiment shown in FIG. 6, the catheter 42 has a thin-walled tubular member 43 formed of polyimide with a balloon element 44 secured by the proximal end thereof to the distal end of the polyimide tubular member 43. A guide element 45 extends through the interior of tubular member 43 and balloon 44 and projects out of the distal end of the balloon. The distal end of the balloon 44 is sealed about the guide element 45 to prevent the loss of inflation fluid. However, a means (not shown) is provided to vent air from the interior of balloon 44 through the distal end of the catheter such as is described in copending application Ser. No. 000,651, Filed Jan. 6, 1987, assigned to the present assignee. A helical coil 47 is disposed about the portion of the guide element 45 which projects out of the distal end of the balloon element 44 and it is secured thereto at location 48 by brazing, soldering, or other suitable means to the plug 49. The distal tip of guide element 45 is also secured to plug 49. The embodiment shown in FIG. 7 is essentially the same as that shown in FIG. 6, except that the guide element 45 is secured to the distal end of tubular member 43 by an adhesive or other suitable means.

In the embodiments shown in FIGS. 6 and 7, the flattened distal portion 50 of the guide element 45 extends to and is secured to the plug 49. If desired, the distal tip of the catheter 42 may be of floppy construction wherein the distal end of the guide element 45 terminates short of the distal tip of the coil 47 and a shaping ribbon (not shown) may extend to the plug 49.

The use of the dilatation catheter described herein generally may follow conventional procedures, with the added advantage of being able to be advanced much further into a patient's vasculature and to cross much tighter lesions than prior dilatation catheters.

While the invention has been described herein in terms of dilatation catheters, the invention can be employed with diagnostic and other types of vascular catheters which are advanced over guidewires through a patient's vascular system. Other modifications and improvements can be made without departing from the scope of the invention.

What is claimed is:

1. A steerable low-profile dilatation catheter, comprising:
    (a) an elongated tubular member formed of polyamide having a wall thickness less than about 0.003 inch and inner lumen extending therethrough;
    (b) an inflatable balloon element, the proximal end of which is secured to the distal end of the thin-walled tubular member with the balloon interior being in fluid communication with the inner lumen of the tubular member to provide inflation fluid thereto;
    (c) a guide element supported within the catheter extending through the interior of the balloon and out the distal end thereof;

(d) means to seal the distal end of the balloon about the guide element to prevent the loss of inflation fluid from the balloon interior; and (e) a helical coil disposed about and secured to the distal portion of the guide element which extends out of the distal end of the balloon.

2. The steerable low-profile dilatation catheter of claim 1 wherein the wall thickness is less than about 0.0015 inch.

3. The steerable low-profile dilatation catheter of claim 1 wherein the inner diameter of the polyimide tubular member is less than 0.015 inch.

4. The steerable low-profile dilatation catheter of claim 1 wherein the guide element extends through the length of the tubular member.

5. The steerable low-profile dilatation catheter of claim 1 wherein the guide element is secured to the distal end of the tubular member.

6. A dilatation catheter comprising:

(a) an elongated tubular member, a substantial portion of which is formed of polyamide, having a wall thickness less than about 0.003 inch an inner lumen extending therethrough;

(b) an inflatable balloon member, the proximal end of which is secured to the distal end of the thin-walled tubular member with the balloon interior being in fluid communication with the inner lumen of the thin-walled tubular member to provide inflation fluid thereto;

(c) an elongated inner member extending through the interior of the inflatable balloon member and out the distal end thereof; and (d) means to seal the distal end of the balloon member about the portion of the elongated inner member extending through the interior of the balloon member to prevent the loss of inflation fluid from the balloon interior.

7. The dilatation catheter of claim 6 wherein the tubular member has a wall thickness of less than about 0.0015 inch.

8. The dilatation catheter of claim 6 wherein the elongated inner member has an inner lumen extending therethrough.

9. The dilatation catheter of claim 8 wherein the elongated inner member has an axial opening in the distal end thereof.

10. The dilatation catheter of claim 6 wherein the elongated inner member is a guiding member with a distal portion thereof extending through the distal end of the balloon member.

11. The dilatation catheter of claim 10 wherein a helical coil is mounted about the distal portion of the guiding member which extends out the distal end of the balloon member.

* * * * *